United States Patent [19]

Ueda

[11] Patent Number: 5,240,732
[45] Date of Patent: Aug. 31, 1993

[54] PLANT EXTRACT-CONTAINING BEVERAGE

[75] Inventor: Shuichiro Ueda, Tokyo, Japan

[73] Assignee: Kabushiki Kaisha Yakult Honsha, Tokyo, Japan

[21] Appl. No.: 795,548

[22] Filed: Nov. 21, 1991

[51] Int. Cl.$^5$ ............................................. A23F 3/18
[52] U.S. Cl. ........................................ 426/597; 426/435
[58] Field of Search ................ 426/590, 592, 597, 435

[56] References Cited

U.S. PATENT DOCUMENTS

| | | | |
|---|---|---|---|
| 3,531,296 | 9/1970 | Smithies | 426/435 |
| 4,051,267 | 9/1977 | Jongeling | 426/597 |
| 4,163,807 | 8/1979 | Jackman | 426/599 |
| 4,311,720 | 1/1982 | Marmo | 426/597 |
| 4,683,140 | 7/1987 | Kang | 426/597 |
| 4,748,033 | 5/1988 | Syfert | 426/597 |
| 4,851,252 | 7/1989 | Greither | 426/597 |

FOREIGN PATENT DOCUMENTS

| | | | |
|---|---|---|---|
| 0437840A1 | 7/1991 | European Pat. Off. | |
| 2910265A1 | of 1979 | Fed. Rep. of Germany. | |
| 89/06966 | 8/1989 | Hungary | 426/597 |
| 59-44028 | 10/1984 | Japan | 426/597 |
| 59-205967 | 11/1984 | Japan | 426/597 |
| 62-171662 | 7/1987 | Japan | 426/597 |
| 62-269642 | 11/1987 | Japan | 426/597 |
| 797642 | 1/1981 | U.S.S.R. | 426/597 |
| 1009394 | 4/1983 | U.S.S.R. | 426/597 |

OTHER PUBLICATIONS

Shokuh Kako yo Tennenbutsu Benran (A Handbook of Natural Products For Food Processing) 9th Edition, published by Shokuhin Kogaku Co. Ltd. p. 335 (1986).
Shin Kanmiyro Gijutsu Shiryo Shu (New Sweetener Technical Data) by Nakayama (editor), Daiichi International Co. Ltd. pp. 193–220 (1987).
World Patent Index Latest Derwent Publications Ltd., London, GB, accession No. 92-092881, week 9212; & JP-A-4036172 (Yakuly Honska K.K.) (1992) abstract.

*Primary Examiner*—Carolyn Paden
*Attorney, Agent, or Firm*—Nixon & Vanderhye

[57] ABSTRACT

A plant extract-containing beverage is provided by this invention which comprises at least one flavonoid-containing plant extract selected from the group consisting of ginkgo leaf extract, persimmon leaf extract, crataegus extract, Japanese pagoda extract and lycium fruit extract, xanthan gum, and water, and further as optional components, a sugar alcohol, at least one usual beverage component and ethanol. The plant extract-containing beverage of the invention contains the various herb crude drugs such as ginkgo leaf extract in a stable state.

3 Claims, No Drawings

PLANT EXTRACT-CONTAINING BEVERAGE

BACKGROUND OF THE INVENTION

This invention relates to a novel plant extract-containing beverage, and relates more detailedly to a beverage containing a flavonoid-containing plant extract selected from the group consisting of ginkgo (*Ginkgo biloba*) leaf extract, persimmon leaf extract, crataegus extract, Japanese pagoda (*Sophora japonica*) extract and lycium fruit extract.

Flavonoid-containing plant extracts such as ginkgo leaf extract, persimmon leaf extract, crataegus extract, Japanese pagoda extract and lycium fruit extract have been utilized from long ago as a herb crude drug. Thus various beverages to which they are added are expected to become healthy beverages. However, all the above flavonoids are liable to form turbidity and precipitates are formed by long-term preservation, and thus a countermeasure is necessary for stability enhancement. Heretofore, there have been carried out as countermeasures for the prevention of turbidity and precipitation in such beverages ① centrifugation treatment, ② filtration treatment, ③ enzymatic treatment ④ compulsory precipitation with a coagulant, ⑤ heightening of the viscosity of products, etc., and actually these means are combined in many cases.

However, even if a precipitate immediately after the preparation can be removed by centrifugation, secondary turbidity and precipitation occuring during preservation cannot be prevented. Further in case of the filtration treatment, secondary precipitation cannot be prevented by filtration accuracy in a degree such that only an initial precipitate is removed. When accurate filtration such as ultrafiltration using an ultrafilter is carried out, the formation of a secondary precipitate is fairly reduced, but at the same time there arises a problem that effective components are removed, too. The enzymatic treatment and the compulsory precipitation treatment with a coagulant take many costs on chemicals to be used such as the enzyme or coagulant, the treatments take a long time, and thus the costs are expensive and moreover the loss of the effective ingredients is large.

By the method to heighten the viscosity of products, precipitation may be prevented but turbidity is difficult to prevent, and moreover, in case of plant extract-containing beverages, refreshing feeling is spoiled and the heightening of the viscosity becomes a strong minus factor for functional aspects.

SUMMARY OF THE INVENTION

Thus this invention aims at providing a beverage containing a flavonoid-containing plant extract and being stabilized by a means free of loss accompanying the stabilization and not spoiling the flavor of the plant extract-containing beverage.

This invention which succeeded in attaining the above object relates to a plant extract-containing beverage comprising at least one flavonoid-containing plant extract selected from the group consisting of ginkgo leaf extract, persimmon leaf extract, crataegus extract, Japanese pagoda extract and lycium fruit extract, xanthan gum, and water; and a beverage wherein a sugar alcohol is further added to this plant extract-containing beverage.

It was ascertained that xanthan gum specifically and sufficiently prevents the precipitation of and turbidity due to the flavonoids in the beverage without having no bad influence lowering organoleptic evaluation, such as viscosity increase.

Further, by raising the Brix degree by adding a sugar alcohol, the above action of xanthan gum becomes surer (refer to the later experimental examples).

Detailed Description of the Invention

As flavonoid-containing extracts to be contained in the beverage of this invention, there can be mentioned ginkgo leaf extract and persimmon leaf extract both containing in a large amount flavonoids such as quercetin and Kaempferol, crataegus (*Crategus cuneata*) extract containing quercetin in a large amount, Japanese pagoda (*Sophora japonica*) extract and lycium fruit extract both containing rutin (a flavonoid) in a large amount, and so on.

These extracts are prepared by extracting such a plant or part thereof with water or aqueous ethanol, and concentrating and, if necessary, further drying the extract to give tinctures, fluidextracts, pilular extracts, powdered extracts, etc., and are sold on the market. Any of these extracts can be used in the beverage of the invention. Their proper addition amounts are as an ultimate concentration on the order of 0.01 to 0.5 g/dl in case of ginkgo leaf extract, on the order of 0.02 to 1.0 g/dl in case of persimmon leaf extract, on the order of 0.05 to 5.0 g/dl in case of crataegus extract, on the order of 0.02 to 2.0 g/dl in case of Japanese pagoda extract, and on the order of 0.02 to 3.0 g/dl in case of lycium fruit extract.

The definition of tincture, fluidextract, pilular extract, powdered extract, etc. depends on Japanese Pharmacopoeia, 12th Revision, but the definitions of these extracts in pharmacopoeias of other countries such as Pharmacopoeia of the United States of America and European Pharmacopoeia are generally nearly alike as in the Japanese Pharmacopoeia, and thus even in case where the definitions depend on pharmacopoeia in other countries, the addition amounts of these extracts may generally be the same as above.

As for xanthan gum to be used in the beverage of the invention, those usually available on the market, for example, Sunace (Sanei Kagaku Co., Ltd,) and Neosoft XR (Taiyo Kagaku Co., Ltd.) can be used as they are. The addition amount of xanthan gum is preferably about 0.005 to 0.08 g/dl, particularly preferably 0.01 to 0.03 g/dl as an ultimate concentration in the beverage. When the addition amount is below 0.005 g/dl, the addition effect may be insufficient, and when the addition amount goes beyond 0.08 g/dl, the beverage may come to have a taste undesirable as a beverage.

Further, examples of the sugar alcohol are sorbitol, maltitol, hydrogenated glucose syrup and hydrogenated starch hydrolyzate, and a mixture thereof, and so on. Desirably, the sugar alcohol is added in an amount such that the Brix of the beverage becomes on the order of 20 to 30. When Brix as the addition amount is below 20, the addition effect may be insufficient, and when it goes beyond 30, diarrhea may sometimes be caused. Examples of commercial products of the hydrogenated glucose syrup are PO-30, PO-40, PO-60, Amameel, Amulty syrop, Amulty, etc., and an example of commercial products of the hydrogenated starch hydrolyzate is PO-20 (All the exemplified products are produced by Towa Kasei Co., Ltd.).

The beverage of the invention can optionally contain, besides the above components, at least one of usual components contained in usual beverages such as, for example, so-called a refreshing beverage, a nutritious beverage, and a healthy beverage (or functional beverage) (a beverage is generally meant drunk by healthy persons for maintaining their health) and a beverage hitting the popular fancy. Examples of such usual beverage components are a sweetener (e.g., fructose glucose liquid sugar, sucrose and licorice extract, etc. and further the above sugar alcohols can also act as a sweetener), a fruit juice (e.g., Japanese apricot juice, apple juice, prune juice, pineapple juice, date juice, etc.), a sour agent (e.g., citric acid, sodium citrate, malic acid, succinic acid, etc.), a perfume (e.g., herb flavor, liqueur flavor, etc.), a coloring agent (e.g., caramel), a vitamin (e.g., ascorbic acid, sodium ascorbate, vitamin $B_1$, $B_2$ or $B_6$, vitamin E, etc.) carbon dioxide when a carbonic beverage is aimed, etc, but they are not essential components for the invention and should not be construed limitatively.

The beverage of the invention generally belongs to usual beverages such as, for example, a refreshing beverage, a nutritions beverage, a healthy or functional beverage and a beverage hitting the popular fancy. The beverage of the invention is usually a nonalcoholic beverage not containing ethanol or containing only a little (e.g. below 1 v/v %) ethanol but may be a so-called alcoholic beverage containing more ethanol. Thus, although the solvent in the beverage of the invention is water, a small amount of ethanol may, in addition, be utilized. Further, usually the beverage of the invention is not a beverage for medical use, but if a beverage belongs to a beverage for medical use, such a beverage falls within this invention so long as it is included in the range of the later claims of the invention.

In preparing the beverage of the invention, when the flavonoid-containing extract is water soluble, all the beverage components may be added all at once to water. However, when the flavonoid-containing extract is water insoluble or sparingly soluble in water, it is possible to obtain a stable dissolution state easily by previously dissolving the extract in a small amount of ethanol or aqueous ethanol and then mixing the solution with the other beverage components.

This invention is specifically described below by experimental examples and examples.

EXPERIMENTAL EXAMPLE 1

Water was added to 100 mg of lycium fruit pilular extract (produced by Nippon Funmatsu Yakuhin Co., Ltd.), 50 mg of licorice fluidextract (Nippon Funmatsu Yakuhin Co., Ltd.), 100 mg of ascorbic acid, 250 mg of a sour agent (200 mg of citric acid +50 mg of sodium citrate), 0.2 ml of a perfume and 28 g of hydrogenated starch hydrolyzate (PO-20, Towa Kasei Co., Ltd.), the mixture was stirred, and the total volume was adjusted to 99 ml with water. The mixture was suction filtered with a filter having a pore size of 8 μm, and 1 ml of a polysaccharide solution was added to the filtrate to obtain a plant extract-containing beverage.

The above preparation process was repeated with various changes of the polysaccharide or without use of any polysaccharides. Brix values of the resulting plant extract-containing beverages were substantially the same and 21, respectively. The beverages were allowed to stand at 30° C. for 2 weeks, and then the occurrence of precipitation and turbidity were observed with the naked eye. The results are shown in Table 1. It was ascertained from Table 1 that xanthan gum is specifically effective, among the polysaccharides, for the prevention of precipitation and turbidity ("−" means no occurrence, and the occurrence becomes clearer as the number of "+" increases)

TABLE 1

| Polysaccharide and its untimate concentration in the beverage | Precipitation | Turbidity |
| --- | --- | --- |
| No addition | ++ | ++ |
| Xanthan gum (0.01 g/dl) (Sanei Kagaku Co., Ltd.) | − | − |
| Gum arabic (0.2 g/dl) (Kyowa Koryo Co., Ltd.) | ++ | ± |
| Tamarind gum (0.04 g/dl) (Dainippon Pharmaceutical Co., Ltd.) | ++ | ± |
| H.M pectin (0.04 g/dl) (SNOW BRAND FOOD CO., LTD.) | ++ | ± |
| Dextrin (0.2 g/dl) (Matsutani Kagaku Co., Ltd.) | ++ | ++ |
| Polydextrose (0.2 g/dl) (Pfeither Co.) | ++ | ++ |
| Sunfiber (0.2 g/dl) (Taiyo Kagaku Co., Ltd.) | − | ++ |
| Cyclodextrin (0.2 g/dl) (Nipon Shokuhin Kako Co., Ltd.) | ++ | ++ |

EXPERIMENTAL EXAMPLE 2

Water was added to 50 mg of ginkgo leaf powdered extract (Japan Green Wave Co., Ltd.), 50 mg of lycium fruit pilular extract (Nippon Funmatsu Yakuhin Co., Ltd.), 20 mg of licorice pilular extract (Nippon Funmatsu Yakuhin Co., Ltd.), 100 mg of ascorbic acid, 250 mg of a sour agent (200 mg of citric acid +50 mg of sodium citrate) and 32 g of hydrogenated starch hyrolyzate (PO-20, Towa Kasei Co., Ltd.) and 10 mg of xanthan gum (Sanei Kagaku Co., Ltd.) to make the whole volume 100 ml, whereby a plant extract-containing beverage was prepared having a Brix value of 24. The ginkgo leaf powdered extract was previously dissolved in 1 ml of 50% ethanol and then mixed with the other components. For comparison, a plant extract-containing beverage was prepared in the same manner as above except for no addition of xanthan gum.

The same preservation test as in Experimental example 1 was conducted to obtain the following results.

| | Precipitation | Turbidity |
| --- | --- | --- |
| Example product | + | + |
| Comparative example product | +++ | +++ |

EXPERIMENTAL EXAMPLES 3 TO 19

A plant extract selected from the group consisting of 40 mg of ginkgo leaf powdered extract (Japan Grean Wave Co., Ltd.), 100 mg of persimmon leaf pilular extract (Hasegawa Koryo Co., Ltd.), 0.5 ml of crataegus fluidextract (Ogawa Koryo Co., Ltd.), 100 mg of lycium fruit pilular extract (Nippon Funmatsu Yakuhin Co., Ltd.) and 100 mg of Japanese pagoda fluidextract (Hasegawa Koryo Co., Ltd.), 199 mg of ascorbic acid, and 250 mg of a sour agent (200 mg of citric acid +50 mg of sodium citrate) were used as basal components. To the basal components was added 10 mg of xanthan gum (Sanei Kagaku Co., Ltd.) alone or together with 38 g of a hydrogenated starch hydrolyzate (PO-20, Towa Kasei Co., Ltd.), and water was further added to make the whole volume 100 ml, whereby a beverage was prepared.

The resulting beverages, having the substantially same Brix value of 28, were subjected to a preservation test by allowing them to stand at 30° C. for 2 weeks. The results are shown in Table 2.

TABLE 2

| Experimental example | plant extract | Xanthan gum | Hydrogenated starch hydrolyzate | Turbidity |
| --- | --- | --- | --- | --- |
| 3 | Lycium fruit | Not added | Not added | ± |
| 4 | Lycium fruit | Added | Not added | − |
| 5 | Lycium fruit | Added | Added | − |
| 6 | Ginkgo leaf | Not added | Not added | ++++ |
| 7 | Ginkgo leaf | Added | Not added | +~++ |
| 8 | Ginkgo leaf | Added | Added | −~± |
| 9 | Lycium fruit + Ginkgo leaf | Added | Not added | +++ |
| 10 | Lycium fruit + Ginkgo leaf | Added | Added | ± |
| 11 | Crataegus | Not added | Not added | + |
| 12 | Crataegus | Added | Not added | − |
| 13 | Crataegus | Added | Added | − |
| 14 | Persimmon leaf | Not added | Not added | ++ |
| 15 | Persimmon leaf | Added | Not added | + |
| 16 | Persimmon leaf | Added | Added | − |
| 17 | Japanese pagoda | Not added | Not added | + |
| 18 | Japanese pagoda | Added | Not added | − |
| 19 | Japanese pagoda | Added | Added | − |

As is seen from the results of the Experimental examples, healthy plant extract-containing beverages are provided by this invention wherein various herb crude drugs such as ginkgo leaf extract are contained in a stable state.

EXAMPLE 1

200 mg of ginkgo leaf powdered extract is dissolved in 10 g of a 50% ethanol solution. Separately, 500 g of water is added to 200 mg of xanthan gum, which is then dissolved with a high speed mixer. With this solution are admixed 380 g of a hydrogenated starch hydrolyzate, and then the above solution of ginkgo leaf powdered extract. 2.5 g of sodium citrate and 2 g of herb flavor are added to the resulting solution, and water is added to make the total volume 1,000 ml. The resulting solution is sterilized at 80° to 95° C. for about one minute, charged into a vessel and cooled to give a beverage having a Brix value of 28 wherein the crude drug is stably contained.

EXAMPLE 2

200 mg of xanthan gum is dissolved in 500 g of water using a high speed mixer. 250 g of a hydrogenated starch hydrolyzate and 130 g of starch syrup are added to and mixed with the solution. To this is added a solution obtained by dissolving 500 mg of ginkgo leaf powdered extract in 30 g of 59% ethanol. Further, 500 mg of lycium fruit fluidextract, 200 mg of licorice fluidextract, 1 g of ascorbic acid, 2.5 g of a sour agent (2.0 g of citric acid + 500 mg of sodium citrate), and 2 g of herb flavor are added, and then water is added to make the total volume 1,000 ml. The resulting solution is filtered with a filter paper of 10 microns, and the filtrate is sterilized at 80° to 95° C. for about one minute, charged into a vessel and cooled to give a beverage having a Brix value of 28 wherein the crude drugs are stably contained.

EXAMPLE 3

200 mg of xanthan gum is added to 500 g of water and the mixture is homogenized with a homogenizer. To this are added 1 g of lycium fruit fluidextract, 1 g of crataegus fluidextract, 200 mg of persimmon leaf fluidextract, 2.5 g of a sour agent (2.0 g of citric acid + 500 mg of sodium citrate), 130 g of fructose glucose liquid sugar and 3 g of herb flavor, and further, water is added to make the total volume 1,000 ml. The resulting solution is filtered with a filter of 10 microns, and the filtrate is sterilized at 80° to 95° C. for about one minute, charged into a vessel and then cooled to give a beverage having a Brix value of 10 wherein the crude drugs are stably contained.

What is claimed is:

1. A beverage containing a flavonoid plant extract consisting essentially of an aqueous solution of:
   (a) a plant extract in an amount of final concentration in g/dl selected from the group consisting of:

| | |
| --- | --- |
| ginkgo leaf | 0.01–0.5 |
| persimmon leaf | 0.02–1.0 |
| crataegus | 0.05–5.0 |
| Japanese pagoda | 0.02–2.0 |
| lycium fruit | 0.02–3.0 |

(b) xanthan gum in a final concentration of 0.01 to 0.03 g/dl, and
   (c) a sugar alcohol in an amount to provide the aqueous solution with a Brix value of 20–30.

2. The beverage of claim 1 further including:
   (d) a plant extract solubilizing amount of ethanol of less than 1 v/v %.

3. The beverage of claim 1 wherein the sugar alcohol is at least one member of the group consisting of sorbitol, maltitol, hydrogenated glucose syrup and hydrogenated starch hydrolyzate.

* * * * *